US012766320B2

(12) United States Patent
Modilevsky et al.

(10) Patent No.: US 12,766,320 B2
(45) Date of Patent: Oct. 20, 2026

(54) CHANGING THE ORIENTATION OF TUMOR TREATING FIELDS (TTFIELDS) BY ADJUSTING THE AMPLITUDES OF TWO OR MORE ELECTRIC FIELDS THAT ARE ALL IN-PHASE WITH EACH OTHER

(71) Applicant: Novocure GmbH, Root (CH)

(72) Inventors: Michael Modilevsky, Haifa (IL); Yevgeniy Telepinsky, Haifa (IL); Michael Krinitsky, Haifa (IL)

(73) Assignee: Novocure GmbH, Baar (CH)

( * ) Notice: Subject to any disclaimer, the term of this patent is extended or adjusted under 35 U.S.C. 154(b) by 260 days.

(21) Appl. No.: 18/374,082

(22) Filed: Sep. 28, 2023

(65) Prior Publication Data

US 2024/0108892 A1 Apr. 4, 2024

Related U.S. Application Data

(60) Provisional application No. 63/411,810, filed on Sep. 30, 2022.

(51) Int. Cl.
*A61N 1/04* (2006.01)
*A61N 1/36* (2006.01)

(52) U.S. Cl.
CPC ........... *A61N 1/36002* (2017.08); *A61N 1/04* (2013.01)

(58) Field of Classification Search
CPC ........ A61N 1/36002; A61N 1/04; A61N 1/06; A61N 1/40
See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 7,599,745 | B2 | 10/2009 | Palti |
| 7,599,746 | B2 | 10/2009 | Palti |
| 7,706,890 | B2 | 4/2010 | Palti |

(Continued)

FOREIGN PATENT DOCUMENTS

| | | | |
|---|---|---|---|
| CN | 113599703 | A | 11/2021 |
| CN | 113616922 | A | 11/2021 |

OTHER PUBLICATIONS

International Search Report and Written Opinion issued in application No. PCT/IB2023/059695 dated Dec. 22, 2023.

*Primary Examiner* — Niketa Patel
*Assistant Examiner* — Joshua Brendon Solomon
(74) *Attorney, Agent, or Firm* — Potomac Law Group, PLLC

(57) ABSTRACT

Tumor Treating Fields (TTFields) therapy is a proven approach for treating tumors using alternating electric fields. When treating tumors in certain anatomic locations (e.g., at certain locations within a subject's head) it may be beneficial to induce an electric field through the subject's body with an overall directionality that varies between more than two directions. The embodiments described herein can induce electric fields in many different directions by simultaneously applying AC signals to different pairs of transducer arrays and adjusting the amplitudes of those AC signals.

16 Claims, 5 Drawing Sheets

(56) References Cited

U.S. PATENT DOCUMENTS 7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Palti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
10,779,875 B2 9/2020 Palti et al.
10,967,167 B2 4/2021 Hagemann et al.
11,103,698 B2 8/2021 Chang et al.
11,191,956 B2 12/2021 Giladi et al.
11,395,916 B2 7/2022 Wasserman et al.
2004/0176804 A1 9/2004 Palti
2005/0209642 A1 9/2005 Palti
2006/0167499 A1 7/2006 Palti
2006/0276858 A1 12/2006 Palti
2007/0225766 A1 9/2007 Palti
2007/0239213 A1 10/2007 Palti
2008/0004675 A1 1/2008 King et al.
2009/0076366 A1 3/2009 Palti
2012/0029419 A1 2/2012 Palti
2012/0283726 A1 11/2012 Palti
2014/0330268 A1 11/2014 Palti et al.
2017/0120041 A1 5/2017 Wenger et al.
2017/0215939 A1 8/2017 Palti et al.
2017/0281934 A1 10/2017 Giladi et al.
2018/0001075 A1 1/2018 Kirson et al.
2018/0008708 A1 1/2018 Giladi et al.
2018/0050200 A1 2/2018 Wasserman et al.
2018/0160933 A1 6/2018 Urman et al.
2018/0202991 A1 7/2018 Giladi et al.
2018/0280687 A1 10/2018 Carter et al.
2019/0117956 A1 4/2019 Wenger et al.
2019/0117963 A1 4/2019 Travers et al.
2019/0117970 A1 4/2019 Schmidt et al.
2019/0224474 A1 7/2019 Yang et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1 3/2020 Naveh et al.
2020/0078582 A1 3/2020 Alon et al.
2020/0108031 A1 4/2020 Borst et al.
2020/0114141 A1 4/2020 Bomzon et al.
2020/0114142 A1 4/2020 Bomzon et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269037 A1 8/2020 Hagemann et al.
2020/0269041 A1 8/2020 Zeevi et al.
2020/0269042 A1 8/2020 Giladi et al.
2020/0368525 A1 11/2020 Maag et al.
2021/0031031 A1 2/2021 Wasserman et al.
2021/0038584 A1 2/2021 Voloshin-Sela
2021/0060334 A1 3/2021 Avraham et al.
2021/0069503 A1 3/2021 Tran et al.
2021/0138233 A1 5/2021 Deslauriers
2021/0162228 A1 6/2021 Urman et al.
2021/0177492 A1 6/2021 Travers et al.
2021/0187277 A1 6/2021 Wasserman et al.
2021/0196348 A1 7/2021 Wasserman
2021/0196967 A1 7/2021 Carlson et al.
2021/0199640 A1 7/2021 Patel et al.
2021/0203250 A1 7/2021 Wasserman
2021/0268247 A1 9/2021 Story et al.
2021/0299439 A1 9/2021 Shamir et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0408383 A1 12/2021 Kalra et al.
2022/0088403 A1 3/2022 Voloshin-Sela et al.
2022/0095997 A1 3/2022 Wasserman
2022/0096821 A1 3/2022 Kirson et al.
2022/0096829 A1 3/2022 Farber et al.
2022/0118249 A1 4/2022 Bomzon et al.
2022/0161028 A1 5/2022 Giladi et al.
2022/0193435 A1 6/2022 Wasserman et al.
2022/0203111 A1 6/2022 Carlson
2022/0267445 A1 8/2022 Tran et al.
2022/0280787 A1 9/2022 Bomzon et al.
2022/0288395 A1 9/2022 Voloshin-Sela et al.
2022/0313992 A1 10/2022 Wasserman
2022/0323753 A1 10/2022 Voloshin-Sela et al.
2022/0387784 A1 12/2022 Kirson et al.
2022/0395699 A1 12/2022 Doyle
2022/0409893 A1 12/2022 Wasserman et al.
2023/0000384 A1 1/2023 Wasserman et al.
2023/0001197 A1 1/2023 Wasserman et al.
2023/0001221 A1 1/2023 Farber
2023/0009366 A1 1/2023 Voloshin-Sela et al.
2023/0019638 A1 1/2023 Wasserman
2023/0037806 A1 2/2023 Wasserman et al.
2023/0043071 A1 2/2023 Wasserman et al.
2023/0098801 A1 3/2023 Carlson
2023/0141087 A1 5/2023 Giladi et al.
2023/0149708 A1 5/2023 O'Connell et al.
2023/0168242 A1 6/2023 Sarkisian et al.
2023/0188055 A1 6/2023 Wasserman
2023/0191123 A1 6/2023 Wasserman et al.
2023/0201616 A1 6/2023 Carlson
2023/0218912 A1 7/2023 Giladi et al.
2023/0241374 A1 8/2023 Shnaiderman et al.
2023/0248826 A1 8/2023 Giladi et al.
2023/0248969 A1 8/2023 Wasserman et al.
2023/0310848 A1 10/2023 Voloshin-Sela et al.
2023/0310849 A1 10/2023 Wasserman et al.
2023/0310877 A1 10/2023 Giladi

CHANGING THE ORIENTATION OF TUMOR TREATING FIELDS (TTFIELDS) BY ADJUSTING THE AMPLITUDES OF TWO OR MORE ELECTRIC FIELDS THAT ARE ALL IN-PHASE WITH EACH OTHER

CROSS REFERENCE TO RELATED APPLICATIONS

This application claims the benefit of U.S. Provisional Application 63/411,810, filed Sep. 30, 2022, which is incorporated herein by reference in its entirety.

BACKGROUND

Tumor Treating Fields (TTFields) therapy is a proven approach for treating tumors using alternating electric fields at frequencies between 50 kHz and 1 MHz (e.g., 150-200 kHz). In the prior art Optune® system, TTFields are delivered to patients via four transducer arrays that are placed on the patient's skin near the tumor. The transducer arrays are arranged in two pairs, with one pair of transducer arrays positioned to the left and right of the tumor, and the other pair of transducer arrays positioned anterior and posterior to the tumor. Each transducer array is connected via a multi-wire cable to an AC signal generator. The AC signal generator (a) sends an AC current through the left/right (L/R) pair of transducer arrays for 1 second, which induces an electric field with a first direction through the tumor; then (b) sends an AC current through the anterior/posterior (A/P) pair of arrays for 1 second, which induces an electric field with a second direction through the tumor; then repeats steps (a) and (b) for the duration of the treatment. Each transducer array includes a plurality (e.g., between 9 and 30) of electrode elements.

Alternating electric fields can also be used to treat medical conditions other than tumors. For example, as described in U.S. Pat. No. 10,967,167 (which is incorporated herein by reference in its entirety), alternating electric fields can be used to increase the permeability of the blood brain barrier (BBB) so that, e.g., chemotherapy drugs can reach the brain.

FIG. 1 depicts the AC signal generator 12 of the prior art Optune® system, and FIG. 2 is a schematic representation of the top view of the Optune® system's A/P and L/R transducer arrays 10 positioned on a person's head. Notably, in the prior art Optune® system, only one of the outputs Q1, Q2 is active at any given instant. When output Q1 is active, the AC signal generator 12 sends an AC current through the L/R pair of transducer arrays, and an electric field with field lines 21 is induced through the tumor (as seen in the left half of FIG. 2). And when output Q2 is active, the AC signal generator 12 sends an AC current through the A/P pair of transducer arrays, and an electric field with field lines 22 is induced through the tumor (as shown in the right half of FIG. 2).

FIG. 3 is a schematic representation of the overall directionality of the electric fields 21, 22 shown in FIG. 2. More specifically, when output Q1 is active (and the AC signal generator 12 is sending an AC current through the L/R pair of transducer arrays 10L/10R), an electric field with a first overall direction 31 is induced. And when output Q2 is active (and the AC signal generator 12 is sending an AC current through the A/P pair of arrays 10A/10P), an electric field with a second overall direction 32 is induced.

Notably, when the prior art Optune® AC signal generator 12 is used together with the prior art transducer arrays 10, only the two overall directions depicted in FIG. 3 are obtainable, and it is not possible to induce an electric field with different overall directionality (e.g., a diagonal orientation) through the subject's head.

SUMMARY OF THE INVENTION

One aspect of the invention is directed to a first method of applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side. The first method comprises inducing a first component of an electric field by applying a first AC signal between the first set of one or more first electrode elements and the second set of one or more second electrode elements and inducing a second component of an electric field by applying a second AC signal between the third set of one or more third electrode elements and the fourth set of one or more fourth electrode elements. The first and second AC signals are applied simultaneously, and the first and second AC signals are in phase with each other. The first method also comprises varying an amplitude of at least one of the first AC signal and the second AC signal over time such that an orientation of an alternating electric field formed by superposition of the first component and the second component varies over time.

Some instances of the first method further comprise positioning the first set of one or more first electrode elements on the first side of the target region; positioning the second set of one or more second electrode elements on the second side of the target region; positioning the third set of one or more third electrode elements on the third side of the target region; and positioning the fourth set of one or more fourth electrode elements on the fourth side of the target region. Optionally, all of the electrode elements are capacitively coupled to the subject's body.

Some instances of the first method further comprise positioning the first set of one or more first electrode elements on the first side of the target region; positioning the second set of one or more second electrode elements on the second side of the target region; positioning the third set of one or more third electrode elements on the third side of the target region; and positioning the fourth set of one or more fourth electrode elements on the fourth side of the target region. All of the electrode elements are conductively coupled to the subject's body.

In some instances of the first method, the varying comprises varying the amplitudes of both the first AC signal and the second AC signal over time so that that the orientation of the alternating electric field rotates. In some instances of the first method, the varying comprises varying the amplitude of at least one of the first AC signal and the second AC signal over time so that the orientation of the alternating electric field oscillates back and forth.

In some instances of the first method, the varying comprises repeating the following steps in an alternating sequence at least 1000 times: setting the amplitudes of the first AC signal and the second AC signal so that the amplitude of the first AC signal is greater than the amplitude of the second AC signal; and setting the amplitudes of the first AC signal and the second AC signal so the amplitude of the second AC signal is greater than the amplitude of the first AC signal.

In some instances of the first method, the varying comprises repeating the following steps in an alternating sequence at least 1000 times: increasing the amplitude of the first AC signal from a minimum value to a maximum value; and decreasing the amplitude of the first AC signal from a maximum value to a minimum value.

Some instances of the first method further comprise inducing a third component of an electric field by applying a third AC signal between a fifth set of one or more fifth electrode elements positioned on a fifth side of the target region and a sixth set of one or more sixth electrode elements positioned on a sixth side of the target region that is opposite to the fifth side. In these instances, the first, second, and third AC signals are all applied simultaneously, and the first, second, and third AC signals are all in phase with each other. An amplitude of the first, second, and third AC signals are varied over time such that an orientation of a vector representing a superposition of the first component, the second component, and the third component varies over time in more than two dimensions.

Another aspect of the invention is direct to a first apparatus for applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side. The first apparatus comprises an AC signal generator and a controller. The AC signal generator is configured to apply a first AC signal between the first set of one or more first electrode elements and the second set of one or more second electrode elements and to simultaneously apply a second AC signal between the third set of one or more third electrode elements and the fourth set of one or more fourth electrode elements, wherein the first and second AC signals are in phase with each other, and wherein the AC signal generator is configured to adjust an amplitude of the first AC signal and to adjust an amplitude of the second AC signal based on control signals that arrive at at least one control input. The controller is configured to send a sequence of control signals to the at least one control input, wherein the control signals cause the AC signal generator to vary the amplitude of at least one of the first AC signal and the second AC signal over time so that an orientation of an alternating electric field that is induced in the target region due to (a) application of the first AC signal between the first set of one or more first electrode elements and the second set of one or more second electrode elements and (b) application of the second AC signal between the third set of one or more third electrode elements and the fourth set of one or more fourth electrode elements varies over time.

Some embodiments of the first apparatus further comprise the first set of one or more first electrode elements; the second set of one or more second electrode elements; the third set of one or more third electrode elements; and the fourth set of one or more fourth electrode elements. Optionally, in these embodiments, all of the electrode elements are capacitively coupled to the subject's body.

Some embodiments of the first apparatus further comprise the first set of one or more first electrode elements; the second set of one or more second electrode elements; the third set of one or more third electrode elements; and the fourth set of one or more fourth electrode elements. All of the electrode elements are conductively coupled to the subject's body.

In some embodiments of the first apparatus, the control signals cause the AC signal generator to vary the amplitude of both the first AC signal and the second AC signal over time so that that the orientation of the alternating electric field rotates. In some embodiments of the first apparatus, the control signals cause the AC signal generator to vary the amplitude at least one of the first AC signal and the second AC signal over time so that the orientation of the alternating electric field oscillates back and forth.

In some embodiments of the first apparatus, the control signals cause the AC signal generator to repeat the following steps in an alternating sequence at least 1000 times: setting the amplitudes of the first AC signal and the second AC signal so that the amplitude of the first AC signal is greater than the amplitude of the second AC signal; and setting the amplitudes of the first AC signal and the second AC signal so the amplitude of the second AC signal is greater than the amplitude of the first AC signal.

In some embodiments of the first apparatus, the control signals cause the AC signal generator to repeat the following steps in an alternating sequence at least 1000 times: increasing the amplitude of the first AC signal from a minimum value to a maximum value; and decreasing the amplitude of the first AC signal from a maximum value to a minimum value.

In some embodiments of the first apparatus, the AC signal generator is further configured to apply a third AC signal between a fifth set of one or more fifth electrode elements positioned on a fifth side of the target region and a sixth set of one or more sixth electrode elements positioned on a sixth side of the target region that is opposite to the fifth side, wherein the first, second, and third AC signals are all in phase with each other, and the AC signal generator is further configured to adjust an amplitude of the third AC signal based on additional control signals that arrive at the at least one control input. In these embodiments, the controller is further configured to send the additional control signals to the at least one control input, wherein the control signals and the additional control signals collectively cause the AC signal generator to vary the amplitude of the first, second, and third AC signals over time so that an orientation of an alternating electric field that is induced in the target region due to application of the first, second, and third AC signals varies over time in more than two dimensions.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
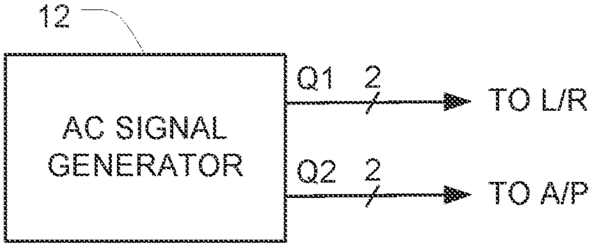
PRIOR ART FIG. 1
FIG. 1 depicts the AC signal generator of the prior art Optune® system.
Figure 2:
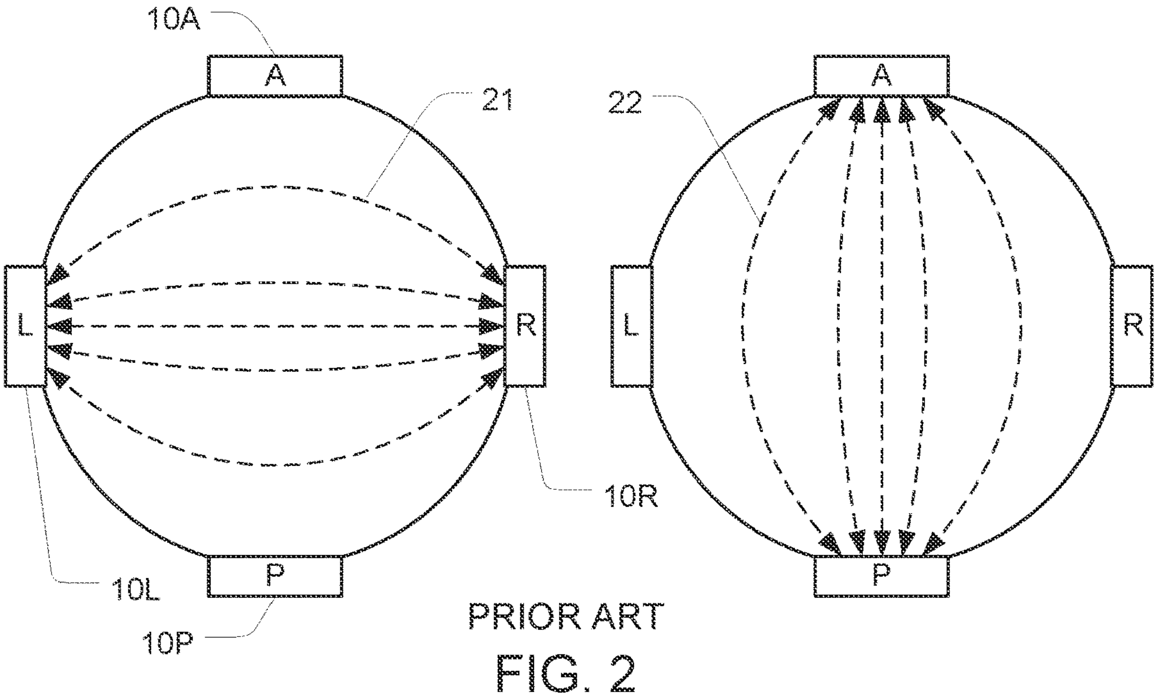
PRIOR ART FIG. 2
FIG. 2 is a schematic representation of the top view of the Optune® system's transducer arrays positioned on a person's head.
Figure 3:
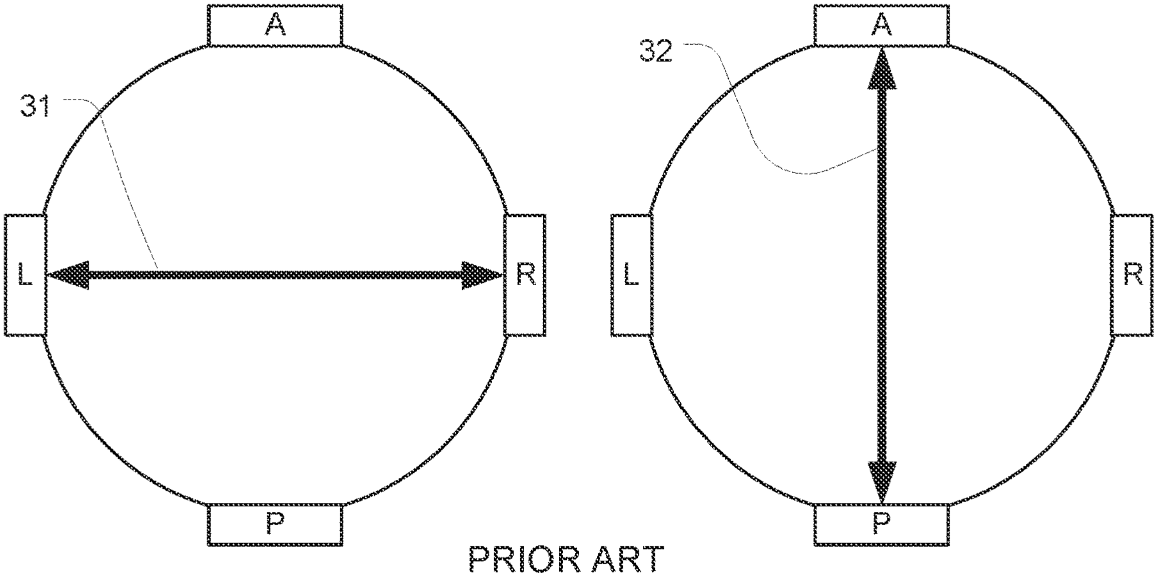
PRIOR ART FIG. 3
FIG. 3 is a schematic representation of the overall directionality of the electric fields shown in FIG. 2.

When treating tumors in certain anatomic locations (e.g., at certain locations within a subject's head) it may be beneficial to induce an electric field through the subject's body with an overall directionality that is different from directions 31 and 32 depicted in FIG. 3. The embodiments described herein can induce electric fields in those different directions by simultaneously applying first and second AC signals that are in-phase with each other to the L/R and A/P pairs of transducer arrays, respectively, and adjusting the amplitudes of those two AC signals.

Figure 4:
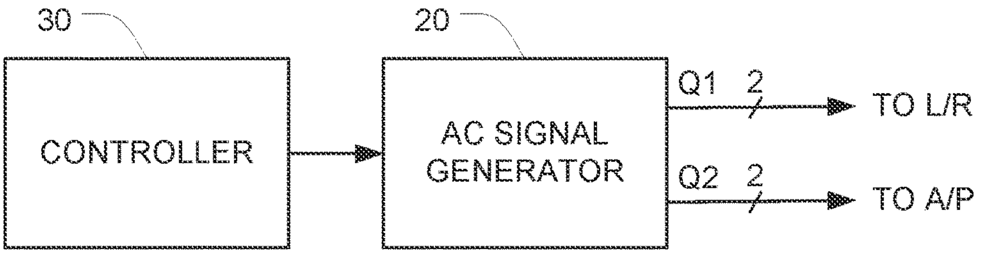
FIG. 4 is a block diagram of a system that can induce electric fields in more than two directions by simultaneously applying AC signals to two or more pairs of transducer arrays.

FIG. 4 is a block diagram of a system that can induce electric fields in more than two directions by simultaneously applying AC signals to two or more pairs of transducer arrays. The system includes an AC signal generator 20 that has two outputs Q1 and Q2. One of those outputs Q1 drives the left and right transducer arrays 10L/10R, and the other output Q2 drives the anterior and posterior transducer arrays 10A/10P. The transducer arrays 10 in this FIG. 4 embodiment are similar to the prior art transducer arrays, and are positioned similarly on the subject's body. Notably, unlike the prior art Optune® system in which only one output of the AC signal generator 12 is active at any given instance, both outputs Q1, Q2 of the AC signal generator 20 in the FIG. 4 embodiment can be active simultaneously. The amplitudes of these outputs Q1, Q2 are individually adjustable, and the AC signal generator 20 is configured to individually adjust these outputs Q1, Q2 based on commands received from a controller 30.

We will now examine what happens in a number of situations when the amplitude of the outputs Q1, Q2 of the AC signal generator 20 are set to different levels.

Figure 5:
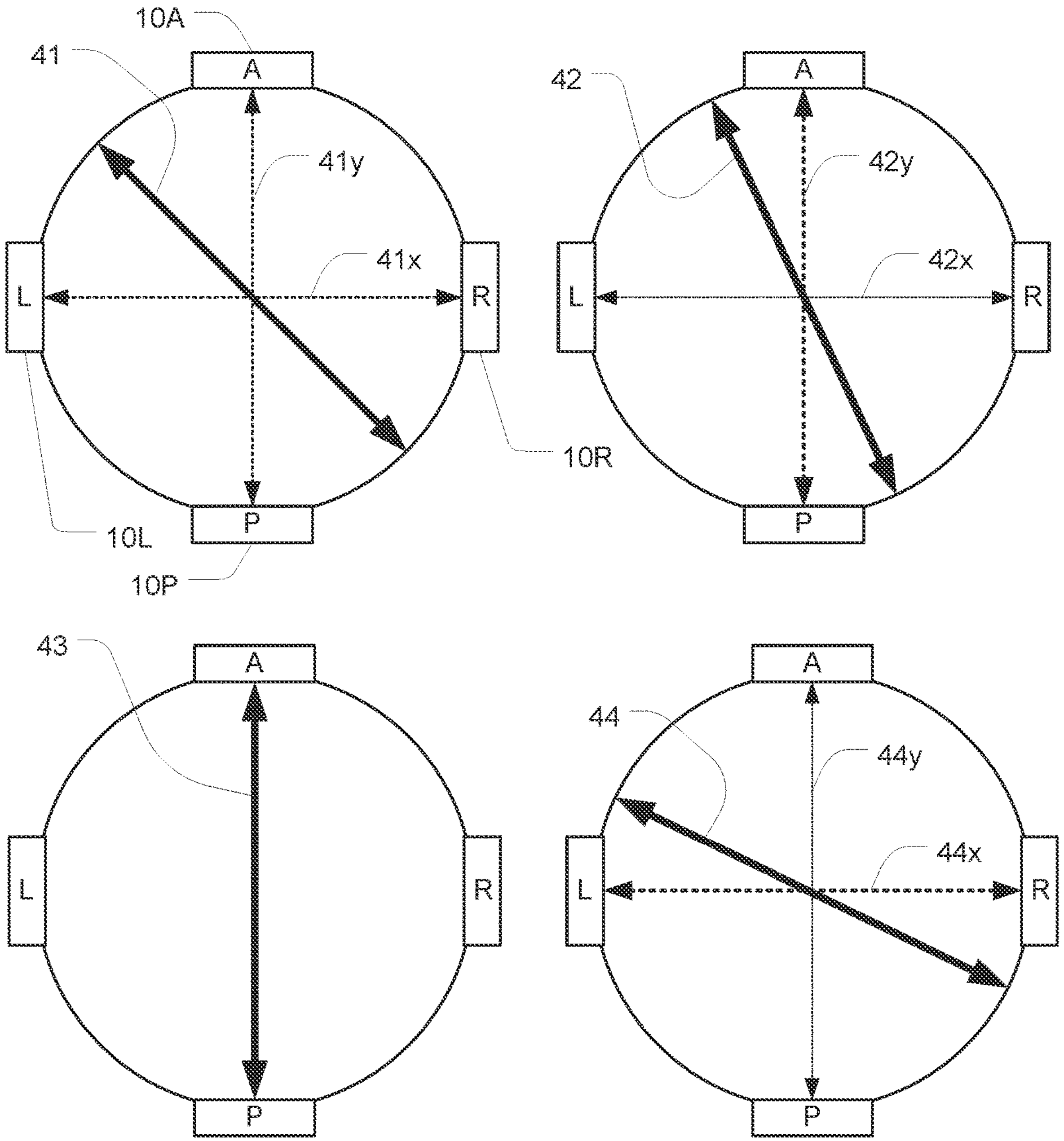
FIG. 5 depicts four examples of how the overall directionality of the electric field can vary when using the FIG. 4 embodiment.

The top left quadrant of FIG. 5 depicts the overall directionality of the electric field that is induced through the subject's body when both outputs Q1 and Q2 of the AC signal generator 20 are active simultaneously at the same amplitude. In this situation, a first AC signal that is applied to the left and right transducer arrays 10L, 10R will induce a first component of an electric field with an overall directionality 41*x*, and a second AC signal that is applied to the anterior and posterior transducer arrays 10A, 10P will induce a second component of an electric field with an overall directionality 41*y*. The first and second AC signals are applied simultaneously via Q1 and Q2 and are in phase with each other. In this situation, the orientation of an alternating electric field that will be induced in the subject's body is formed by superposition of the first component 41*x* and the second component 41*y*, and the resulting superposition will have the overall directionality 41 for the reasons explained in more detail below in connection with FIG. 6.

The top right quadrant of FIG. 5 depicts the overall directionality of the electric field that is induced through the subject's body when both outputs Q1 and Q2 of the AC signal generator 20 are active simultaneously, but the amplitude of Q1 is half the amplitude of Q2. In this situation, a first AC signal that is applied to the left and right transducer arrays 10L, 10R will induce a first (smaller) component of an electric field with an overall directionality 42*x*, and a second AC signal that is applied to the anterior and posterior transducer arrays 10A, 10P will induce a second (larger) component of an electric field with an overall directionality 42*y*. The first and second AC signals are applied simultaneously via Q1 and Q2 and are in phase with each other. In this situation, the orientation of an alternating electric field that will be induced in the subject's body is formed by superposition of the first component 42*x* and the second component 42*y*, and the resulting superposition will have the overall directionality 42 for the reasons explained in more detail below in connection with FIG. 7.

The lower left quadrant of FIG. 5 depicts the overall directionality of the electric field that is induced through the subject's body when only output Q2 of the AC signal generator 20 is active, and the amplitude of output Q1 is set to zero. In this situation, no signal is applied to the left and right transducer arrays 10L, 10R, and an AC signal is applied only to the anterior and posterior transducer arrays 10A, 10P. This will induce an electric field with an overall directionality 43 for the reasons explained in more detail below in connection with FIG. 8. (Note that this yields an end result that is similar to the situation described above in connection with the right half of FIG. 3.)

The lower right quadrant of FIG. 5 depicts the overall directionality of the electric field that is induced through the subject's body when both outputs Q1 and Q2 of the AC signal generator 20 are active simultaneously, but the amplitude of Q1 is twice the amplitude of Q2. In this situation, a first AC signal that is applied to the left and right transducer arrays 10L, 10R will induce a first (larger) component of an electric field with an overall directionality 44*x*, and a second AC signal that is applied to the anterior and posterior transducer arrays 10A, 10P will induce a second (smaller) component of an electric field with an overall directionality 44*y*. The first and second AC signals are applied simultaneously via Q1 and Q2 and are in phase with each other. Once again, the orientation of an alternating electric field that will be induced in the subject's body is formed by superposition of the first component 44*x* and the second component 44*y*, and the resulting superposition will have the overall directionality 44.

Note that while the top left, top right, and lower right quadrants of FIG. 5 each depicts the situation in which the two components (e.g., 41*x* and 41*y* in the top left quadrant) that ultimately add by superposition into a resulting sum with an overall directionality (e.g., 41 in the top left quadrant) are orthogonal. But orthogonality is not a prerequisite for the two components to add by superposition. Therefore, even if the L/R pair of electrodes is offset from orthogonal with respect to the A/P pair of electrodes, the components that are attributable to each of those pairs of electrodes will still add by superposition into a sum that has a single overall directionality. The math for computing the resulting field direction will, however, be somewhat more difficult in order to account for any offset from orthogonality.

Figure 6:
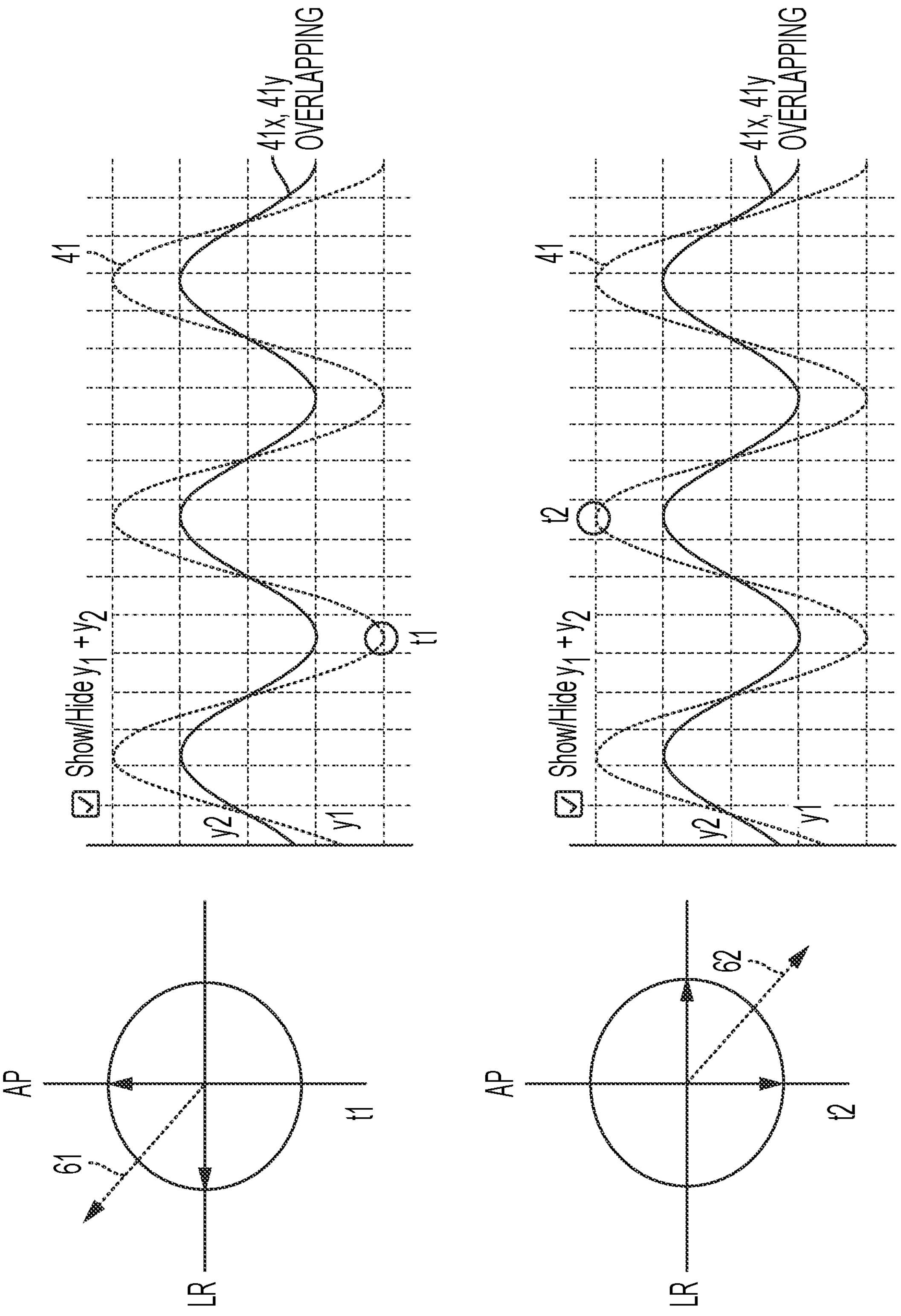
FIG. 6 depicts additional details that correspond to the top left panel of FIG. 5.

FIG. 6 depicts additional details that correspond to the top left panel of FIG. 5. Because both outputs Q1 and Q2 are in phase and have the same amplitude, the traces for those two outputs 41*x*, 41*y* overlap on FIG. 6. The superposition of those two traces 41*x*, 41*y* results in the trace 41. Notably, at time t1, there is a negative component in the x direction and a negative component in the y direction, which results in an instantaneous superposition 61. Similarly, at time t2, there is a positive component in the x direction and a positive component in the y direction, which results in an instantaneous superposition 62.

Figure 7:
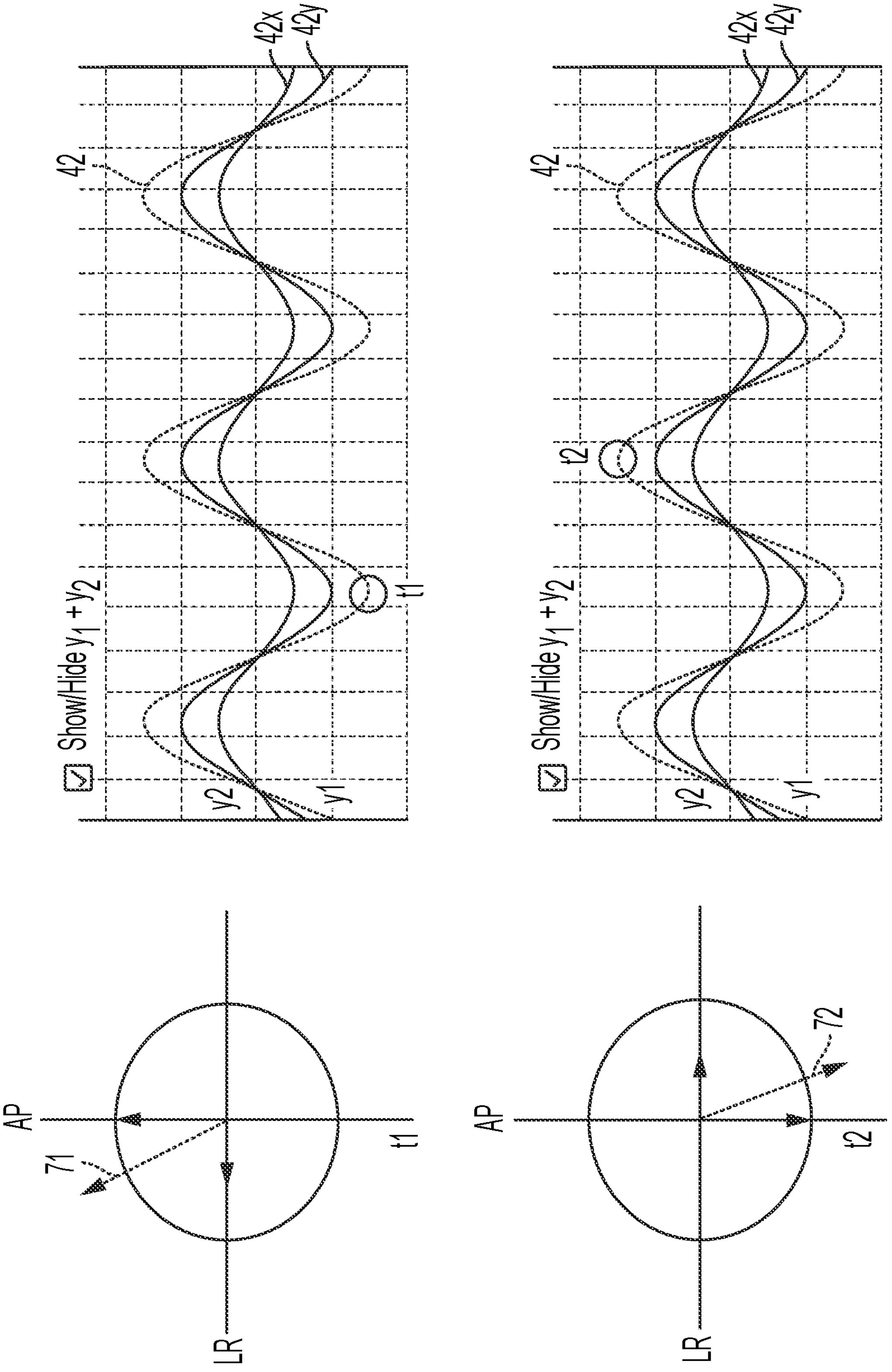
FIG. 7 depicts additional details that correspond to the top right panel of FIG. 5.

FIG. 7 depicts additional details that correspond to the top right panel of FIG. 5, when both outputs are active simultaneously, but the amplitude of Q1 (trace 42*x*) is half the amplitude of Q2 (trace 42*y*). The superposition of those two traces 42*x*, 42*y* results in the trace 42. Notably, at time t1, there is a negative component in the x direction and a larger negative component in the y direction, which results in an instantaneous superposition 71. Similarly, at time t2, there is a positive component in the x direction and a larger positive component in the y direction, which results in an instantaneous superposition 72.

Figure 8:
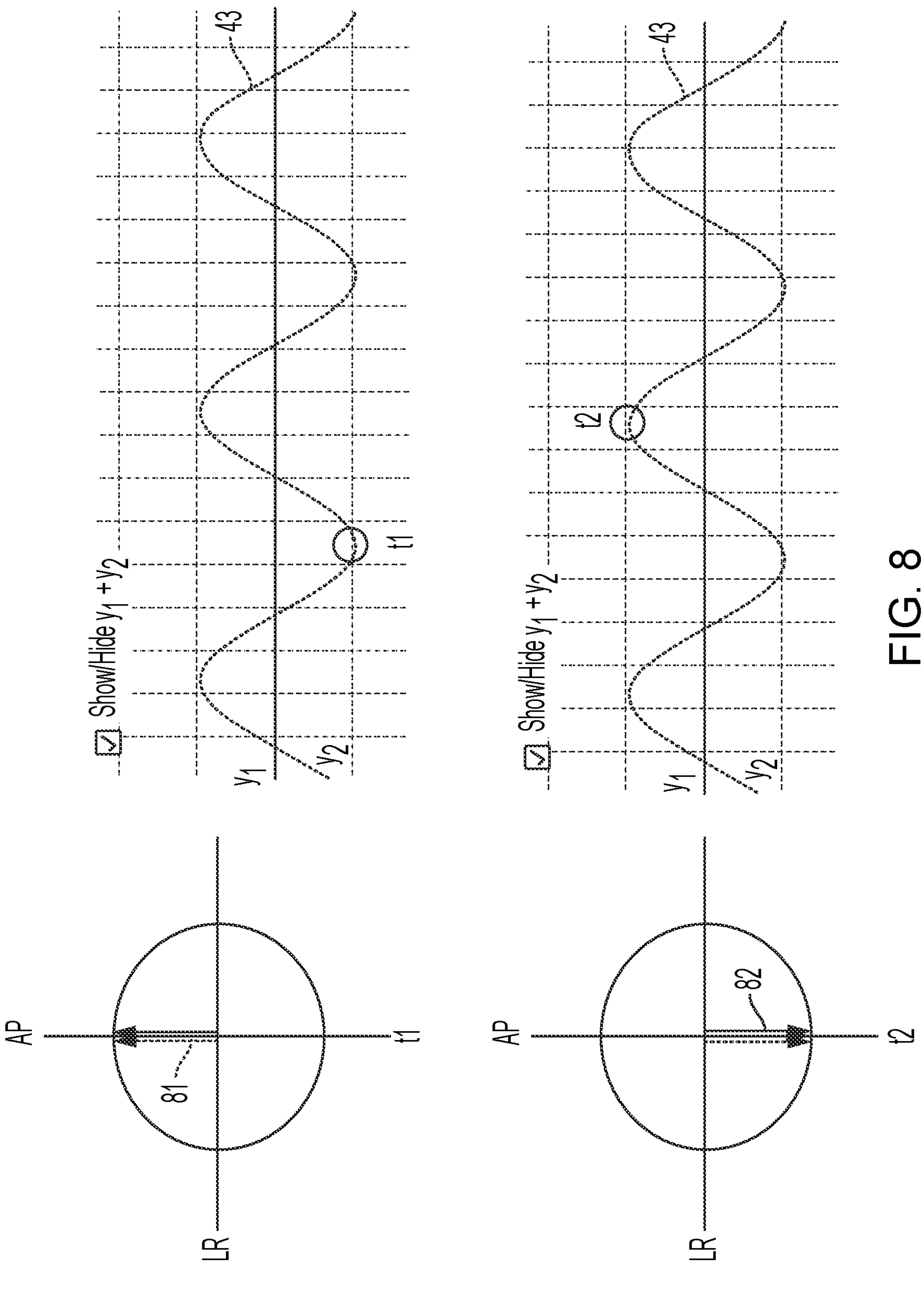
FIG. 8 depicts additional details that correspond to the lower left panel of FIG. 5.

FIG. 8 depicts additional details that correspond to the lower left panel of FIG. 5. In this situation, no signal (i.e., zero amplitude) is applied to the left and right transducer arrays 10L, 10R, so there is no x component. There is only a y component, so the superposition (trace 43) is the same as the y component. Notably, at time t1, there is a negative component in the y direction, which results in an instantaneous superposition 81. Similarly, at time t2, there is a positive component in the y direction, which results in an instantaneous superposition 82.

The ability to steer the overall directionality of the electric field to any desired direction can provide additional flexibility in terms of deciding where to position the transducer arrays on a given subjects body's during a treatment-planning phase that precedes the application of the alternating electric fields. For example, if a large part of a particular subject's forehead is afflicted by a skin condition that makes it painful to position a transducer array there, it could be impossible to generate electric fields in two different directions that are roughly orthogonal using prior art treatment-planning techniques. In contrast, by using the ability to steer the overall directionality of the electric field provided by the embodiments described herein, all four transducer arrays could be evenly distributed around the sides and back of the subject's head, and it will still be possible to generate electric fields in two different directions that are roughly orthogonal (which can provide improved results).

Returning to FIGS. 4 and 5, the apparatus 10, 20 applies an alternating electric field to a target region in a subject's body using a first set of one or more first electrode elements 10L positioned on a first side of the target region, a second set of one or more second electrode elements 10R positioned on a second side of the target region that is opposite to the first side, a third set of one or more third electrode elements 10A positioned on a third side of the target region, and a fourth set of one or more fourth electrode elements 10P positioned on a fourth side of the target region that is opposite to the third side. The apparatus includes an AC signal generator 20 and a controller 30.

The AC signal generator 20 is configured to apply a first AC signal between the first set of one or more first electrode elements 10L and the second set of one or more second electrode elements 10R and to simultaneously apply a second AC signal between the third set of one or more third electrode elements 10A and the fourth set of one or more fourth electrode elements 10P. The first and second AC signals are in phase with each other, and the AC signal generator 20 is configured to adjust an amplitude of the first AC signal and to adjust an amplitude of the second AC signal based on control signals that arrive at at least one control input.

The controller 30 is configured to send a sequence of control signals to the at least one control input, so that the control signals cause the AC signal generator 20 to vary the amplitude of at least one of the first AC signal and the second AC signal over time so that an orientation of an alternating electric field that is induced in the target region due to (a) application of the first AC signal between the first set of one or more first electrode elements 10L and the second set of one or more second electrode elements 10R and (b) application of the second AC signal between the third set of one or more third electrode elements 10A and the fourth set of one or more fourth electrode elements 10P varies over time. (For example, the orientation could vary over time between the situation depicted in the top left panel and top right panels of FIG. 5.)

In some embodiments of the apparatus depicted in FIGS. 4 and 5, each of the first electrode elements is capacitively coupled to the subject's body, each of the second electrode elements is capacitively coupled to the subject's body, each of the third electrode elements is capacitively coupled to the subject's body, and each of the fourth electrode elements is capacitively coupled to the subject's body. In alternative embodiments of the apparatus depicted in FIGS. 4 and 5, each of the first electrode elements is conductively coupled to the subject's body, each of the second electrode elements is conductively coupled to the subject's body, each of the third electrode elements is conductively coupled to the subject's body, and each of the fourth electrode elements is conductively coupled to the subject's body.

In some embodiments of the apparatus depicted in FIG. 4, the control signals generated by the controller 30 cause the AC signal generator 20 to vary the amplitude of both the first AC signal and the second AC signal over time so that that the orientation of the alternating electric field rotates. In alternative embodiments of the apparatus depicted in FIG. 4, the control signals generated by the controller 30 cause the AC signal generator 20 to vary the amplitude at least one of the first AC signal and the second AC signal over time so that the orientation of the alternating electric field oscillates back and forth. In these embodiments, because the overall directionality of the field can be controlled by adjusting the amplitude of the various components that contribute to the field, any desired speed of rotation (or oscillation) of the field can be implemented, including faster rotations/oscillations (e.g., 10 per second), slower rotations/oscillations (e.g., 10 per hour), or anywhere between those two rates. This stands in stark contrast to the situation described in U.S. Pat. No. 7,565,206, which is incorporated herein by reference, in which a rotating field is obtained by applying a sine wave to one pair of transducer arrays and applying a cosine wave to the other pair of transducer arrays, in which case the speed of rotation would be predetermined (and extremely fast).

In some embodiments of the apparatus depicted in FIG. 4, the control signals generated by the controller 30 cause the AC signal generator 20 to repeat the following steps in an alternating sequence at least 1000 times: setting the amplitudes of the first AC signal and the second AC signal so that the amplitude of the first AC signal is greater than the amplitude of the second AC signal; and setting the amplitudes of the first AC signal and the second AC signal so the amplitude of the second AC signal is greater than the amplitude of the first AC signal.

In some embodiments of the apparatus depicted in FIG. 4, the control signals generated by the controller 30 cause the AC signal generator 20 to repeat the following steps in an alternating sequence at least 1000 times: increasing the amplitude of the first AC signal from a minimum value to a maximum value; and decreasing the amplitude of the first AC signal from a maximum value to a minimum value.

Note that in the embodiments described above, the AC signal generator applies signal simultaneously to two pairs of transducer arrays, which changes the overall directionality between the four orientations 41-44 depicted in FIG. 5, and that all four of these overall directions 41-44 are positioned on a single two-dimensional plane. When additional pairs of transducer arrays are provided, the concepts described above can be extended to shift the overall directionality out of that single two-dimensional plane, and into any three dimensional overall directionality that is desired.

This can be accomplished, for example, by configuring the AC signal generator 20 to apply a third AC signal between a fifth set of one or more fifth electrode elements positioned on a fifth side of the target region and a sixth set of one or more sixth electrode elements positioned on a sixth side of the target region that is opposite to the fifth side, wherein the first, second, and third AC signals are all in phase with each other. The AC signal generator 20 is further configured to adjust an amplitude of the third AC signal based on additional control signals that arrive at the at least one control input.

In these three-dimensional embodiments, the controller 30 is further configured to send the additional control signals to the at least one control input, so that the control signals and the additional control signals collectively cause the AC signal generator 20 to vary the amplitude of the first, second, and third AC signals over time so that an orientation of an alternating electric field that is induced in the target region due to application of the first, second, and third AC signals varies over time in more than two dimensions.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side, the method comprising:

inducing a first component of an electric field by applying a first AC signal between the first set of one or more first electrode elements and the second set of one or more second electrode elements;

inducing a second component of an electric field by applying a second AC signal between the third set of one or more third electrode elements and the fourth set of one or more fourth electrode elements, wherein the first and second AC signals are applied simultaneously, and wherein the first and second AC signals are in phase with each other; and varying an amplitude of at least one of the first AC signal and the second AC signal over time such that an orientation of an alternating electric field formed by superposition of the first component and the second component varies over time, wherein the varying comprises repeating the following steps in an alternating sequence at least 1000 times: (a) setting the amplitudes of the first AC signal and the second AC signal so that the amplitude of the first AC signal is greater than the amplitude of the second AC signal and (b) setting the amplitudes of the first AC signal and the second AC signal so the amplitude of the second AC signal is greater than the amplitude of the first AC signal.

2. The method of claim 1, further comprising:

positioning the first set of one or more first electrode elements on the first side of the target region;

positioning the second set of one or more second electrode elements on the second side of the target region;

positioning the third set of one or more third electrode elements on the third side of the target region; and positioning the fourth set of one or more fourth electrode elements on the fourth side of the target region.

3. The method of claim 2, wherein each of the first electrode elements is capacitively coupled to the subject's body, wherein each of the second electrode elements is capacitively coupled to the subject's body, wherein each of the third electrode elements is capacitively coupled to the subject's body, and wherein each of the fourth electrode elements is capacitively coupled to the subject's body.

4. The method of claim 2, wherein each of the first electrode elements is conductively coupled to the subject's body, wherein each of the second electrode elements is conductively coupled to the subject's body, wherein each of the third electrode elements is conductively coupled to the subject's body, and wherein each of the fourth electrode elements is conductively coupled to the subject's body.

5. The method of claim 1, wherein the varying comprises varying the amplitudes of both the first AC signal and the second AC signal over time so that that the orientation of the alternating electric field rotates.

6. The method of claim 1, wherein the varying comprises varying the amplitude of at least one of the first AC signal and the second AC signal over time so that the orientation of the alternating electric field oscillates back and forth.

7. A method of applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side, the method comprising:

inducing a first component of an electric field by applying a first AC signal between the first set of one or more first electrode elements and the second set of one or more second electrode elements;

inducing a second component of an electric field by applying a second AC signal between the third set of one or more third electrode elements and the fourth set of one or more fourth electrode elements, wherein the first and second AC signals are applied simultaneously, and wherein the first and second AC signals are in phase with each other; and varying an amplitude of at least one of the first AC signal and the second AC signal over time such that an orientation of an alternating electric field formed by superposition of the first component and the second component varies over time, wherein the varying comprises repeating the following steps in an alternating sequence at least 1000 times: (a) increasing the amplitude of the first AC signal from a minimum value to a maximum value and (b) decreasing the amplitude of the first AC signal from a maximum value to a minimum value.

8. A method of applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side, the method comprising:

inducing a first component of an electric field by applying a first AC signal between the first set of one or more first electrode elements and the second set of one or more second electrode elements;

inducing a second component of an electric field by applying a second AC signal between the third set of one or more third electrode elements and the fourth set of one or more fourth electrode elements, wherein the first and second AC signals are applied simultaneously, and wherein the first and second AC signals are in phase with each other;

varying an amplitude of at least one of the first AC signal and the second AC signal over time such that an orientation of an alternating electric field formed by superposition of the first component and the second component varies over time; and inducing a third component of an electric field by applying a third AC signal between a fifth set of one or more fifth electrode elements positioned on a fifth side of the target region and a sixth set of one or more sixth electrode elements positioned on a sixth side of the target region that is opposite to the fifth side, wherein the first, second, and third AC signals are all applied simultaneously, and wherein the first, second, and third AC signals are all in phase with each other; and wherein an amplitude of the first, second, and third AC signals are varied over time such that an orientation of a vector representing a superposition of the first component, the second component, and the third component varies over time in more than two dimensions.

9. An apparatus for applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side, the apparatus comprising:

an AC signal generator configured to apply a first AC signal between the first set of one or more first electrode elements and the second set of one or more second electrode elements and to simultaneously apply a second AC signal between the third set of one or more third electrode elements and the fourth set of one or more fourth electrode elements, wherein the first and second AC signals are in phase with each other, and wherein the AC signal generator is configured to adjust an amplitude of the first AC signal and to adjust an amplitude of the second AC signal based on control signals that arrive at at least one control input; and a controller configured to send a sequence of control signals to the at least one control input, wherein the control signals cause the AC signal generator to vary the amplitude of at least one of the first AC signal and the second AC signal over time so that an orientation of an alternating electric field that is induced in the target region due to (a) application of the first AC signal between the first set of one or more first electrode elements and the second set of one or more second electrode elements and (b) application of the second AC signal between the third set of one or more third electrode elements and the fourth set of one or more fourth electrode elements varies over time, wherein the control signals cause the AC signal generator to repeat the following steps in an alternating sequence at least 1000 times:

setting the amplitudes of the first AC signal and the second AC signal so that the amplitude of the first AC signal is greater than the amplitude of the second AC signal; and setting the amplitudes of the first AC signal and the second AC signal so the amplitude of the second AC signal is greater than the amplitude of the first AC signal.

10. The apparatus of claim 9, further comprising:

the first set of one or more first electrode elements;

the second set of one or more second electrode elements;

the third set of one or more third electrode elements; and the fourth set of one or more fourth electrode elements.

11. The apparatus of claim 10, wherein each of the first electrode elements is capacitively coupled to the subject's body, wherein each of the second electrode elements is capacitively coupled to the subject's body, wherein each of the third electrode elements is capacitively coupled to the subject's body, and wherein each of the fourth electrode elements is capacitively coupled to the subject's body.

12. The apparatus of claim 10, wherein each of the first electrode elements is conductively coupled to the subject's body, wherein each of the second electrode elements is conductively coupled to the subject's body, wherein each of the third electrode elements is conductively coupled to the subject's body, and wherein each of the fourth electrode elements is conductively coupled to the subject's body.

13. The apparatus of claim 9, wherein the control signals cause the AC signal generator to vary the amplitude of both the first AC signal and the second AC signal over time so that that the orientation of the alternating electric field rotates.

14. The apparatus of claim 9, wherein the control signals cause the AC signal generator to vary the amplitude at least one of the first AC signal and the second AC signal over time so that the orientation of the alternating electric field oscillates back and forth.

15. The apparatus of claim 9, wherein the AC signal generator is further configured to apply a third AC signal between a fifth set of one or more fifth electrode elements positioned on a fifth side of the target region and a sixth set of one or more sixth electrode elements positioned on a sixth side of the target region that is opposite to the fifth side, wherein the first, second, and third AC signals are all in phase with each other, and wherein the AC signal generator is further configured to adjust an amplitude of the third AC signal based on additional control signals that arrive at the at least one control input; and wherein the controller is further configured to send the additional control signals to the at least one control input, wherein the control signals and the additional control signals collectively cause the AC signal generator to vary the amplitude of the first, second, and third AC signals over time so that an orientation of an alternating electric field that is induced in the target region due to application of the first, second, and third AC signals varies over time in more than two dimensions.

16. An apparatus for applying an alternating electric field to a target region in a subject's body using a first set of one or more first electrode elements positioned on a first side of the target region, a second set of one or more second electrode elements positioned on a second side of the target region that is opposite to the first side, a third set of one or more third electrode elements positioned on a third side of the target region, and a fourth set of one or more fourth electrode elements positioned on a fourth side of the target region that is opposite to the third side, the apparatus comprising:

an AC signal generator configured to apply a first AC signal between the first set of one or more first electrode elements and the second set of one or more second electrode elements and to simultaneously apply a second AC signal between the third set of one or more third electrode elements and the fourth set of one or more fourth electrode elements, wherein the first and second AC signals are in phase with each other, and wherein the AC signal generator is configured to adjust an amplitude of the first AC signal and to adjust an amplitude of the second AC signal based on control signals that arrive at at least one control input; and a controller configured to send a sequence of control signals to the at least one control input, wherein the control signals cause the AC signal generator to vary the amplitude of at least one of the first AC signal and the second AC signal over time so that an orientation of an alternating electric field that is induced in the target region due to (a) application of the first AC signal between the first set of one or more first electrode elements and the second set of one or more second electrode elements and (b) application of the second AC signal between the third set of one or more third electrode elements and the fourth set of one or more fourth electrode elements varies over time, wherein the control signals cause the AC signal generator to repeat the following steps in an alternating sequence at least 1000 times:

increasing the amplitude of the first AC signal from a minimum value to a maximum value; and decreasing the amplitude of the first AC signal from a maximum value to a minimum value.

* * * * *